US00PP08831P

United States Patent [19]

VandenBerg

[11] Patent Number: Plant 8,831

[45] Date of Patent: Jul. 12, 1994

[54] CHRYSANTHEMUM PLANT NAMED EL PASO

[75] Inventor: Cornelis P. VandenBerg, Salinas, Calif.

[73] Assignee: Yoder Brothers, Inc., Barberton, Ohio

[21] Appl. No.: 96,520

[22] Filed: Jul. 26, 1993

[51] Int. Cl.[5] ..... A01H 5/00

[52] U.S. Cl. ..... Plt./79

[58] Field of Search ..... Plt. 78, 79, 76

*Primary Examiner*—Howard J. Locker

*Attorney, Agent, or Firm*—Foley & Lardner

[57] ABSTRACT

A Chrysanthemum plant named El Paso particularly characterized by its flat capitulum form; decorative capitulum type; light bronze flower color; diameter across face of capitulum of 89 to 114 mm when fully opened, when grown as a pinched disbudded pot mum; photoperiodic flowering response to short days of 52 to 59 days; plant height, with 15 to 16 long days after sticking unrooted cuttings, and with 1 to 2 applications of 2500 ppm B-9 SP, ranges from 23 to 28 cm when grown as a pinched pot mum with 4 cuttings in a 15 cm pot; branching pattern is spreading, each plant having 3 to 5 laterals after pinch; and recommended as disbud pot mum.

3 Drawing Sheets

The present invention comprises a new and distinct cultivar of Chrysanthemum, botanically known as *Dendranthema grandiflora,* and referred to by the cultivar name El Paso.

El Paso, identified as 5937 (90-747002), was originated from a cross made by Cornelis P. VandenBerg in a controlled breeding program in Salinas, Calif., in 1990.

The female parent of El Paso was the cultivar identified as Envy, disclosed in U.S. Plant Pat. No. 5,986.

The male parent of El Paso was an unnamed seedling identified as 5047 (87-62202), and described as a decorative disbud pot mum with many disc florets; a golden-yellow ray floret color; a flowering response to short days of 51 to 58 days under normal conditions in Salinas, Calif.; a plant height of 18 to 23 cm with 15 to 16 long days after sticking unrooted cuttings prior to start of short days and 1 to 2 applications of 2500 ppm B-9 SP when grown as a pinched pot mum; branching habit of 3 to 5 laterals developing after pinch; and diameter of capitulum of 114 to 127 mm. The male parent was discarded from all programs on Mar. 4, 1991.

El Paso was discovered and selected as one flowering plant within the progeny of the stated cross by Cornelis P. VandenBerg in December 1990, in a controlled environment in Salinas, Calif.

The first act of asexual reproduction of El Paso was accomplished when vegetative cuttings were taken from the initial selection in March 1991 in a controlled environment in Salinas, Calif., by technicians working under supervision of Cornelis P. VandenBerg.

Horticultural examination of controlled flowerings of successive plantings has shown that the unique combination of characteristics as herein disclosed for El Paso are firmly fixed and are retained through successive generations of asexual reproduction.

El Paso has not been observed under all possible environmental conditions. The phenotype may vary significatnly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of El Paso, which, in combination, distinguish this Chrysanthemum as a new and distinct cultivar:

1. Flat capitulum form.
2. Decorative capitulum type.
3. Light bronze flower color.
4. Diameter across face of capitulum of 89 to 114 mm when fully opened, when grown as a pinched disbudded pot mum.
5. Photoperiodic flowering response to short days of 52 to 59 days.
6. Plant height with 15 to 16 long days after sticking unrooted cuttings, and with 1 to 2 applications of 2500 ppm B-9 SP, ranges from 23 to 28 cm when grown as a pinched pot mum with 4 cuttings in a 15 cm pot.
7. Branching pattern is spreading, each plant having 3 to 5 laterals after pinch.
8. Recommended as disbud pot mum.

The accompanying photographic drawings show typical inflorescence and leaf characteristics of El Paso, with the colors being as nearly true as possible with illustrations of this type.

Sheet 1 is a color photograph of El Paso grown as a pinched disbudded pot mum with 4 cuttings in a 15 cm pot.

Sheet 2 is a black and white photograph of three views of the inflorescence of El Paso.

Sheet 3 is a black and white photograph showing the upper and under sides of the leaves of El Paso at 3 stages of development (mature, intermediate and immature). In sheets 2 and 3 a measuring tape in centimeters has been added.

Of the commercial cultivars know to the inventor, the most similar in comparison to El Paso is the cultivar identified as Dark Bronze Charm, disclosed in U.S. Plant Pat. No. 6,801. Reference is made to attached Chart A, which compares certain characteristics of El Paso to the same characteristics of Dark Bronze Charm.

Similar traits are capitulum form and type, diameter across face of capitulum, plant height and spreading branching pattern. El Paso has a lighter ray floret color than Dark Bronze Charm, and is 2 to 4 days slower in flowering response to short days than Dark Bronze Charm. In several flowering trails El Paso had one less lateral after pinch when compared with Dark Bronze Charm.

In the following description, color references are made to The Royal Horticultural Society Colour Chart. The color values were determined on plant material grown as a pinched disbudded pot mum in Salinas, Calif. on Oct. 26, 1992.

Classification:

*Botanical.*—*Dendranthema grandiflora* cv. El Paso.

*Commercial.*—Decorative disbud pot mum.

INFLORESCENCE

A. Capitulum:

*Form.*—Flat.

*Type.*—Decorative.

*Diameter across face.*—89 to 114 mm when fully opened.

B. Corolla of ray florets:

*Color (general tonality from a distance of three meters).*—Light bronze

*Color (upper surface).*—Closest to 22B to 22C.

*color (under surface).*—Closest to 22D.

*Shape.*—Straight, ribbed, some spoons in outer rows of ray florets.

C. Corolla of disc florets:

*Color (mature).*—7B.

*Color (immature).*—144A to 144B.

D. Reproductive organs:

*Androecium.*—Present on disc florets only; no pollen.

*Gynoecium.*—Present on both ray and disc florets.

PLANT

A. General appearance:

*Height.*—23 to 28 cm when grown as a pinched pot in a 15 cm pot with 15 to 16 long days after direct sticking of unrooted cuttings and 1 to 2 applications of 2500 ppm B-9 SP.

*Branching pattern.*—Spreading, with 3 to 5 laterals after pinch.

B. Foliage:

*Color (upper surface).*—147A.

*Color (under surface).*—147B.

*Shape.*—See photograph.

CHART A

COMPARISON OF EL PASO AND DARK BRONZE CHARM

| CHARACTERISTICS | EL PASO | DARK BRONZE CHARM |
|---|---|---|
| Ray floret color | Light bronze | Orange bronze |
| Capitulum form and type | Flat decorative | Flat decorative |
| Diameter across face of capitulum | 89 to 114 mm | 95 to 114 mm |
| Flowering response | 52 to 59 days | 50 to 55 days |
| Plant height with 15 to 16 long days | 23 to 28 cm | 23 to 28 cm |
| Branching pattern | Spreading 3 to 5 laterals | Spreading 4 to 5 laterals |

COMPARISONS MADE OF PLANTS GROWN AS PINCHED DISBUDDED POT MUMS IN SALINAS, CALIFORNIA

I claim:

1. A new and distinct Chrysanthemum plant named El Paso, as described and illustrated.

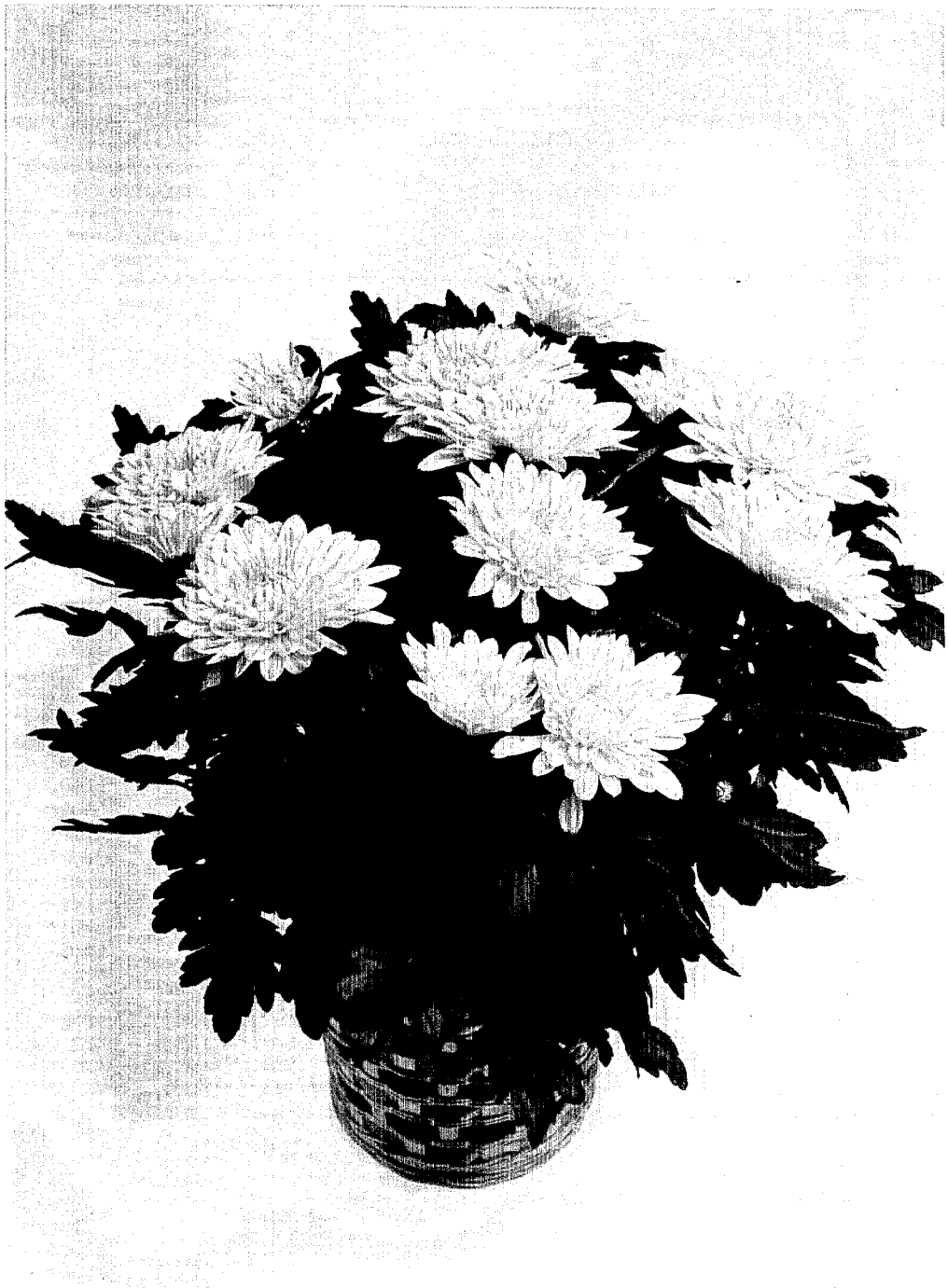

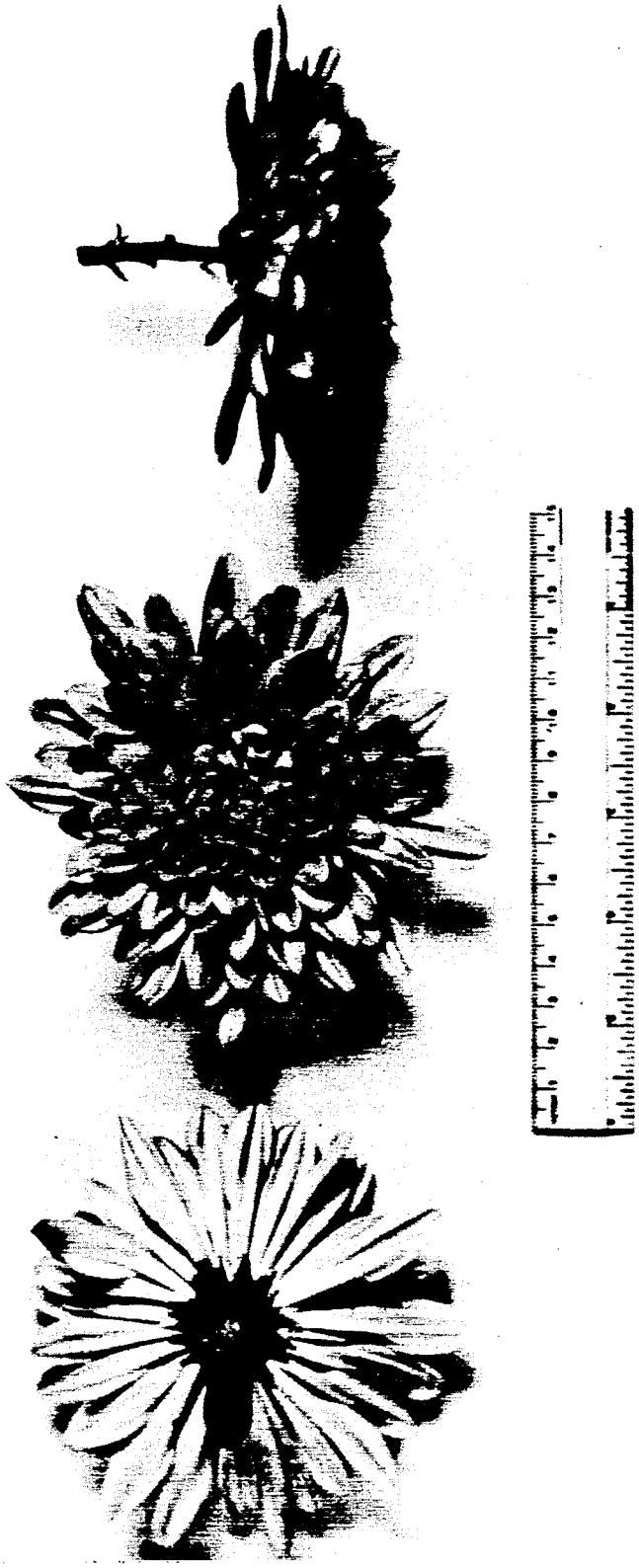

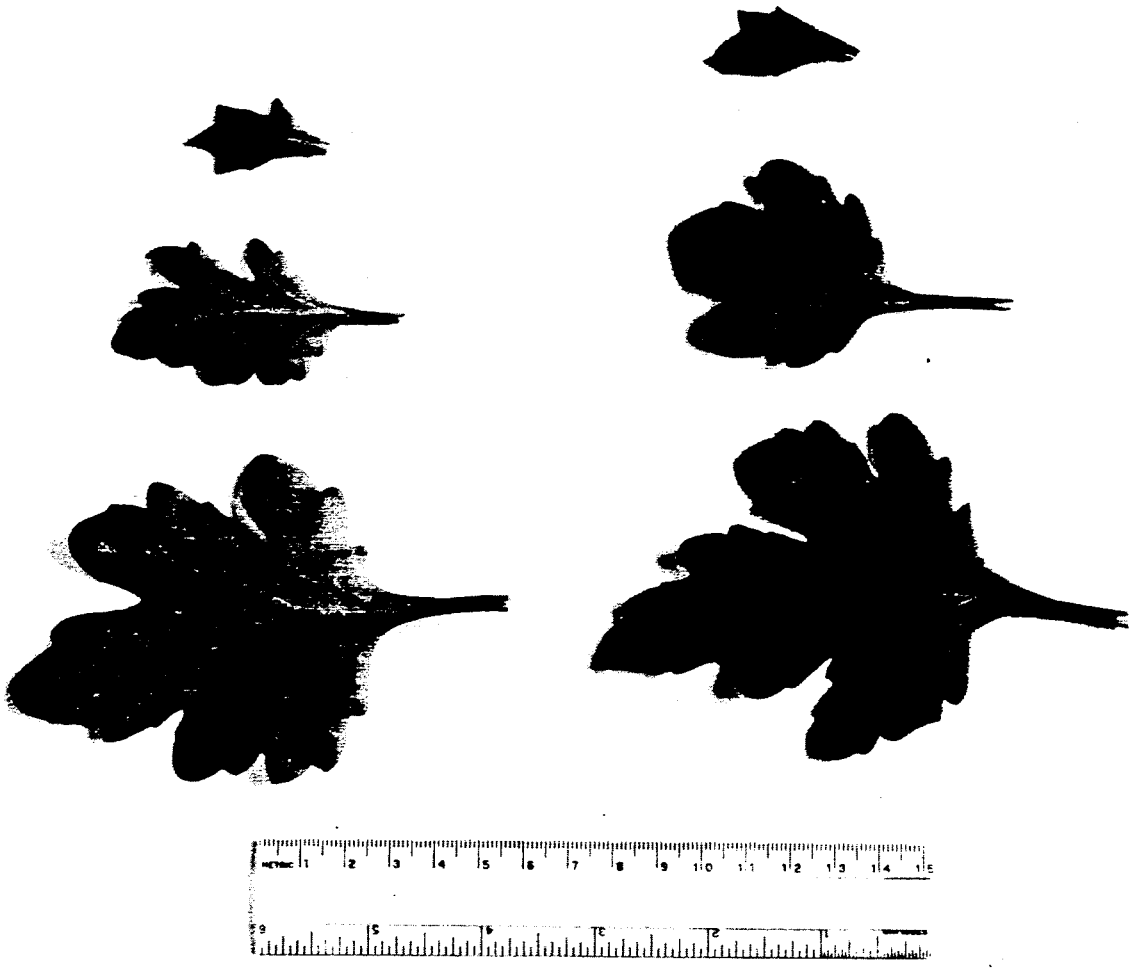

* * * * *